US00PP36890P2

(12) United States Plant Patent
Hansen

(10) Patent No.: US PP36,890 P2
(45) Date of Patent: Aug. 12, 2025

(54) ***EPIMEDIUM* PLANT NAMED 'Wisteria Falls'**

(50) Latin Name: ***Epimedium* hybrid**
Varietal Denomination: Wisteria Falls

(71) Applicant: Hans A. Hansen, Zeeland, MI (US)

(72) Inventor: Hans A. Hansen, Zeeland, MI (US)

( * ) Notice: Subject to any disclaimer, the term of this patent is extended or adjusted under 35 U.S.C. 154(b) by 0 days.

(21) Appl. No.: 18/831,503

(22) Filed: Mar. 5, 2025

(51) Int. Cl.
*A01H 6/00* (2018.01)
*A01H 5/02* (2018.01)

(52) U.S. Cl.
USPC ..... Plt./429

(58) Field of Classification Search
USPC ..... Plt./429
CPC ..... A01H 6/00; A01H 5/02
See application file for complete search history.

*Primary Examiner* — Keith O. Robinson

(57) ABSTRACT

A new cultivar of *Epimedium* plant named 'Wisteria Falls' characterized by its medium size habit and evergreen foliage with flowers on cascading panicles with pinkish lilac sepals, wine-colored petals that deepen in color of the spurs on airy branched panicles beginning in late spring. The foliage is semi-evergreen with three leaflets of light chartreuse with burgundy blush and patterns in cooler conditions and becoming deep green in summer.

1 Drawing Sheet

Botanical denomination: *Epimedium* hybrid.
Variety designation: 'Wisteria Falls'.

STATEMENT REGARDING PRIOR DISCLOSURES UNDER 37 CFR 1.77(B)(6)

The Applicant asserts that no publications or advertisements relating to sales, offers for sale, or public distribution of the new plant occurred more than one year prior to the effective filing date of this application. The first offer for sale was by Walters Gardens, Inc. on Mar. 6, 2024, to Pleasant Run Nursery. Walters Gardens, Inc. obtained the new plant and all information about the new plant directly from the inventor. Any information or disclosure about the claimed plant less than one year prior to the effective filing date of this application would have been obtained from directly or indirectly from the Inventor and would be a 35 U.S.C. 102(b) exception.

BACKGROUND OF THE INVENTION

The present invention relates to a new and distinct Barrenwort plant from the genus *Epimedium* and given the cultivar name 'Wisteria Falls'. The new plant was the result of a single seedling selection from a cross on Apr. 20, 2016, by the inventor between a proprietary hybrid involving *Epimedium acuminatum* assigned the breeder code D-29 (not patented) as the female or seed parent and the proprietary unnamed selection of *Epimedium zhushanense* (not patented) as the male or pollen parent. The seeds were collected in May of 2016. The individually selected seedling was eventually given the breeder code 16-91-94 after being first isolated from trials at a nursery in Zeeland, MI during April of 2018. It was selected for the final introduction in April of 2020.

*Epimedium* 'Wisteria Falls' has been asexually propagated at the same nursery in Zeeland, MI by division of the rhizome in 2018 and found to reproduce plants that are identical and exhibit all the characteristics of the original plant in successive generations of asexual propagation.

*Epimedium* 'Wisteria Falls' has not been observed under all possible environments. The phenotype may vary slightly with different environmental conditions, such as temperature, light, fertility, moisture and maturity levels, but without any change in the genotype.

In comparison to the new plant, the female parent has smaller flowers of lighter pinkish lavender, and the foliage has smaller marginal teeth. The male parent has smaller flowers and fewer flowers per panicle with cream-colored sepals that develop a slight pale pinkish lavender with maturity and petals that become darker purple with maturity.

The nearest comparison varieties known to the inventor are: 'Cranberry Dancer' U.S. Plant Pat. No. 36,548 and 'Hugs and Kisses' U.S. Plant patent application Ser. No. 18/831,502.

'Cranberry Dancer' has a larger habit in both height and width and has large-sized flowers having burgundy spurs with yellowish tips and prominent burgundy sepals with white margins. 'Hugs and Kisses' has flowers with pinkish mauve sepals, deep mauve spurs, and mauve petals that lighten distally with orangish tips. Both 'Cranberry Dancer' and 'Hugs and Kisses' have panicles that are more upright.

*Epimedium* 'Wisteria Falls' is distinct from the parents and all other *Epimedium* known to the inventor in the following combined traits:

1. Compact, dense, semi-evergreen perennial;
2. Flowers on cascading panicles with pinkish lilac sepals, wine-colored petals that deepen in color of the spurs on airy branched panicles beginning in late spring;
3. Foliage is semi-evergreen, lanceolate, light chartreuse with a burgundy blush and patterns in cooler conditions becoming medium green in the heat of summer.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source, and direction may cause the appearance of minor variations in color.

DETAILED PLANT DESCRIPTION

Figure 1:
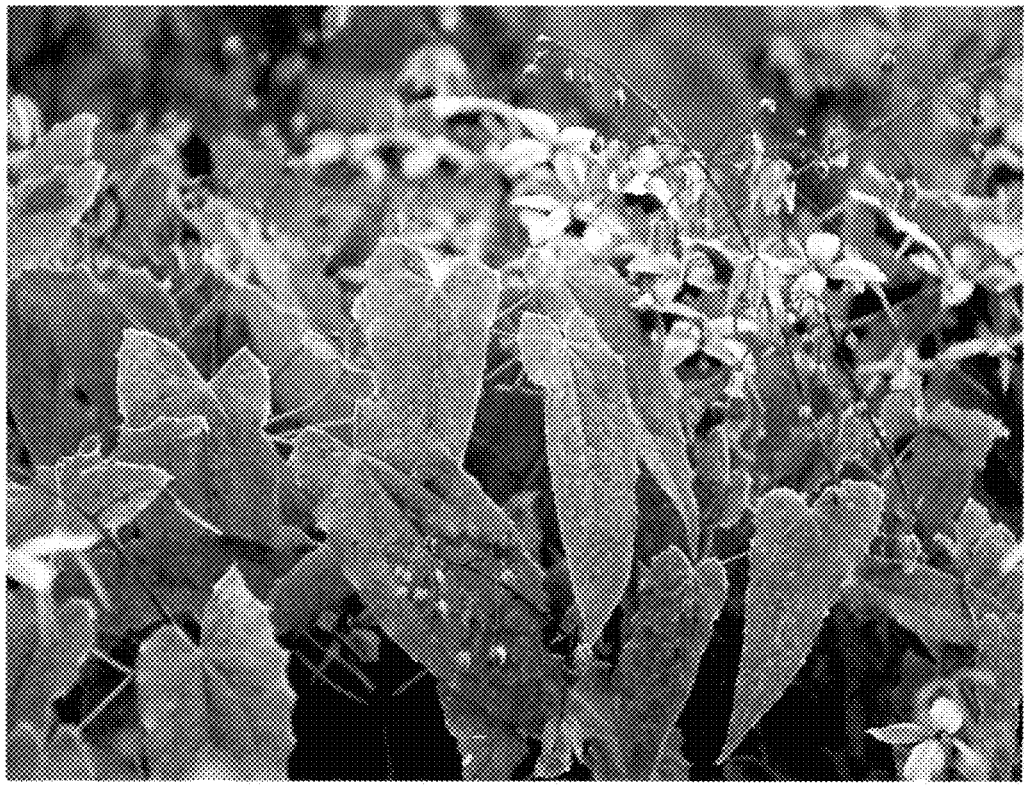
FIG. 1 shows a two-year-old plant in mid-season flower in greenhouse production block at a nursery in Zeeland, Michigan.
Figure 2:
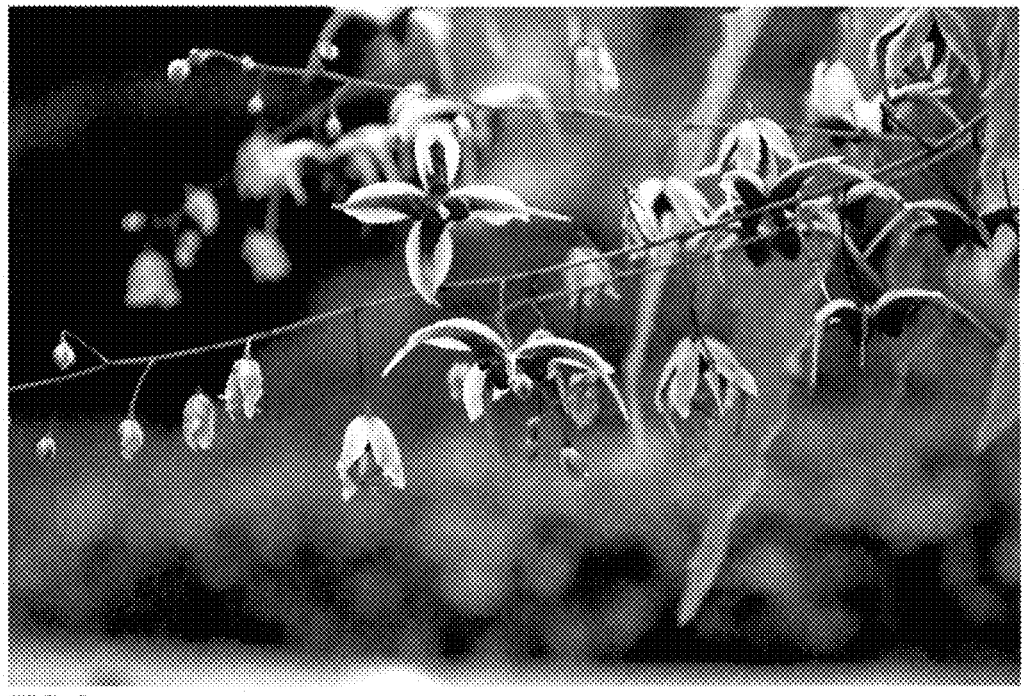
FIG. 2 shows a close-up of the scape with flowers and buds of a two-year-old plant grown in a greenhouse production block at a nursery in Zeeland, Michigan.

The following is a detailed description of the new *Epimedium* cultivar 'Wisteria Falls' based on observations of a two-year old specimen grown in a shaded greenhouse in Zeeland, Michigan with supplemental watering and fertilizer as needed. Color descriptions are from the 2015 edition of The Royal Horticultural Society Colour Chart except where common dictionary terms are used.

Parentage: The female or seed parent is *Epimedium acuminatum* D-29, the male or pollen parent is an unnamed selection of *Epimedium zhushanense;*

Propagation: Rhizome divisions;

Growth rate: Moderate;

Root development: Initiating in about 6 weeks;

Crop time: Finishing in a 3.8-liter pot from a 50 mm plug in 10 to 12 weeks;

Plant size: Soil level to top of foliar plane to about 40 cm tall and to about 60 cm wide, soil level to top of floral plane about 58 cm;

Root description: Dense, fibrous roots on rhizomes; color nearest RHS 161C;

Rhizomes: Surface smooth, matte, glabrous; to about 9 cm in length and 5 mm in width; variable in color distally nearest RHS 60C and proximally between RHS N170D and RHS N155D;

Branching habit: Branches arise from rhizome;

Stem: Cylindrical; moderately glossy; glabrous proximally and sparsely puberulent distally; strong; stiff; about 16 cm in length and 2.5 mm in diameter at base; aspect upwardly in proximal portion and arching distally;

Stem color: Variable; proximally between RHS N179A and RHS 146A, distally nearest RHS 146A with nodes between RHS 147A and RHS N179A;

Stem aspect: Initially upright and arching with maturity;

Internode length: 16 cm;

Leaf: Both cauline and from petiole arising from the soil; typically one per petiole or two to three per cauline node; tri-parted; to 25 cm wide and 20 cm long;

Leaflet: Three; lanceolate; stiff; acute apex; cordate base, not overlapping; slightly undulate; finely serrulate to with stiff, sharply-pointed, small spines to about 2 mm wide and 2 mm long; center leaflet to 19 cm long and 7.5 cm wide, cordate base symmetrical with lobes to 3.5 cm wide and 2 cm long; side leaflets to 19 cm long and 8 cm wide, cordate base obtuse with outer lobe to 4 cm wide and 3.5 cm long, inner lobe to 3.5 cm wide and 1.5 cm long;

Leaflet surface: Adaxial smooth; glabrous; highly lustrous; abaxial densely puberulent and matte;

Leaflet color: Young adaxial between RHS 146C and RHS 146B with area surrounding veins, blush, and irregular small patches 1 mm across to up to 2 cm across of between RHS 187A and RHS N186C, and large regions of nearly 75% of the leaf between RHS 176B and RHS 183B; young abaxial nearest RHS 148B; mature adaxial nearest RHS 137A;, mature abaxial between RHS N138B and N138C;

Leaflet venation: Palmate; adaxial lightly indented and glabrous; abaxial slightly costate and puberulent; color adaxial nearest RHS 137A; color abaxial midrib between RHS 146C and RHS 147C, and primary veins nearest RHS 146C and secondary veins nearest RHS 146A;

Petioles: Arising from rhizome; cylindrical; smooth; slightly lustrous; stiff, wiry; to 20 cm long and 2 mm diameter;

Petiole color: Between RHS 53B and RHS 53A;

Petiolules: Cylindrical; smooth; slightly lustrous; stiff; glabrous; to about 6.5 cm long and 1 mm diameter on center or side leaflets; swollen to about 2 mm diameter in the 2 mm below leaflet blade;

Petiolule color: Between RHS 165C and RHS 152B; swollen portion variable nearest RHS N186B and between RHS 146A and RHS 146B;

Inflorescence: Compound corymb; flowering in the upper 20 cm and to about 16 cm wide; with about 22 branches, branches having up about 7 flowers; inflorescence with about 50 to 60 flowers;

Flower timing: Beginning in late spring for about 3 weeks;

Flower buds one day prior to starting to open: Globose; smooth; glabrous; about 5 mm long and 4 mm diameter;

Bud color one day prior to starting to open: Inner sepals nearest but lighter than both RHS 69D and RHS 75D; outer sepals between RHS 195A and RHS 177D;

Flower: Perfect; complete; actinomorphic; aspect drooping;

Flower size: To about 65 mm in across and 25 mm in depth;

Flower fragrance: None detected;

Lastingness of flowers: About 7 days from initial opening dehiscence; self-cleaning;

Petals: Four; with center spurs; lanceolate; arcuate downwardly and toward center axis; apex narrowly acute; base truncate, adnate on axial portion; adaxial and abaxial smooth, glabrous and slightly lustrous; to about 25 mm long natural, 36 mm long straightened, and about 6 mm across at base, spur portion about 5 mm long and 5 mm across;

Petal color: When opening and fully open adaxial and abaxial spur and proximal adaxial and abaxial petal between RHS N79B and RHS 79B, with distal 5 mm of petal nearest RHS 14D;

Pedicel: Cylindrical; glandular; to about 20 mm long and 0.3 mm diameter; average about 10 mm long and 0.3 mm diameter at base;

Pedicel color: In distal portion of corymb between RHS N179A and RHS 146A, in proximal portion of corymb nearest RHS 146B;

Peduncle: Cylindrical; stiff; strong; wiry; sparsely micro-puberulent; slightly lustrous; with to about 22 branches; peduncle aspect base upright and distally arching, branches outwardly to about 80 degrees below main axis; to about 44 cm long and 2 mm diameter at base; branches to about 10 cm long and 1 mm diameter at base;

Peduncle color: Proximally between RHS N179A and RHS 146A, distally nearest RHS 146A with nodes between RHS 147A and RHS N179A;

Sepals: Four; rotate; single whorl; oblong; smooth; glabrous and matte; truncate base, acute apex; margin entire; to about 20 mm long and 10 mm across;

Sepal color: Adaxial and abaxial between RHS 76C and RHS 75D;

Androecium: Four;

*Anther*.—Four; longitudinal; basifixed; extrose; oblong; to about 3 mm long and 1 mm across; color prior to opening nearest RHS 8B.

*Filaments*.—Four; applanate; about 3.5 mm long and 1 mm wide at base, narrowing distally; color nearest RHS 155C.

*Pollen*.—Abundant; color nearest RHS 5D.

Gynoecium: Single; superior;

*Style*.—Cylindrical; glabrous; about 3 mm long and 0.3 mm diameter; color nearest RHS 187B.

*Stigma*.—Oblong; glabrous; to about 0.1 mm long and about 0.5 mm diameter; color nearest RHS NN155A.

*Ovary*.—Superior; oblong; glabrous; smooth; to about 3 mm long and 1 mm diameter; color between RHS 195B and RHS 160C.

Fruit: Bi-valved capsule; cylindrical; arcuate about 45 to 90 degrees; to about 10 mm long and 2 mm diameter with a 5 mm beak; color while maturing nearest RHS 146B with a blush of nearest 187C;

Seeds: About 10 to 15 per capsule; about 1 mm long and 0.5 mm across; color nearest RHS 157D;

Pests and disease: The new plant has not been tested or shown to be susceptible or resistance to pests and diseases common to *Epimedium*.

Growth: The new plant has survived USDA winter hardiness to at least zones 5 to 8 but has not been tested yet beyond these temperatures.

It is claimed:

1. A new and distinct cultivar of *Epimedium* plant named 'Wisteria Falls' as herein described and illustrated.

* * * * *